(12) United States Patent
Jeon et al.

(10) Patent No.: US 11,458,294 B2
(45) Date of Patent: Oct. 4, 2022

(54) MICROJET DRUG INJECTION DEVICE EQUIPPED WITH BACKFLOW PREVENTION VALVE

(71) Applicant: JSKBIOMED INC., Daejeon (KR)

(72) Inventors: Jin Woo Jeon, Incheon (KR); Jung Kook Kim, Daejeon (KR); Seung Dal Seo, Daejeon (KR); Jun Hak Park, Cheonan-si (KR)

(73) Assignee: JSKBIOMED INC., Daejeon (KR)

( * ) Notice: Subject to any disclaimer, the term of this patent is extended or adjusted under 35 U.S.C. 154(b) by 312 days.

(21) Appl. No.: 16/611,355

(22) PCT Filed: Jul. 3, 2018

(86) PCT No.: PCT/KR2018/007492
§ 371 (c)(1),
(2) Date: Nov. 6, 2019

(87) PCT Pub. No.: WO2019/045247
PCT Pub. Date: Mar. 7, 2019

(65) Prior Publication Data
US 2020/0164198 A1    May 28, 2020

(30) Foreign Application Priority Data

Aug. 31, 2017  (KR) .......................... 10-2017-0111146
Sep. 27, 2017  (KR) .......................... 10-2017-0124913

(51) Int. Cl.
*A61M 39/24*       (2006.01)
*A61M 5/30*        (2006.01)

(52) U.S. Cl.
CPC .......... *A61M 39/24* (2013.01); *A61M 5/3007* (2013.01); *A61M 2039/2406* (2013.01)

(58) Field of Classification Search
CPC .................. A61M 39/24; A61M 39/22; A61M 2039/2406; A61M 2039/2426;
(Continued)

(56) References Cited

U.S. PATENT DOCUMENTS

| 5,261,459 A | * 11/1993 | Atkinson .............. A61M 39/24 |
| | | 137/846 |
| 5,840,061 A | 11/1998 | Menne et al. |

(Continued)

FOREIGN PATENT DOCUMENTS

| CN | 1915444 A | 2/2007 |
| KR | 10-2007-0018725 A | 2/2007 |

(Continued)

OTHER PUBLICATIONS

Office Action for corresponding KR 10-2017-0124913, dated Oct. 24, 2017.
(Continued)

*Primary Examiner* — Kevin C Sirmons
*Assistant Examiner* — Alexandra Lalonde
(74) *Attorney, Agent, or Firm* — Sughrue Mion, PLLC

(57) ABSTRACT

The present invention provides a microjet drug injection device equipped with a backflow prevention valve, the microjet drug injection device comprising an upper housing, a lower housing, a partition, and the backflow prevention valve provided with a slit through which a drug passes at a lower end and allowing the drug to move only towards an injection nozzle.

9 Claims, 9 Drawing Sheets

(58) Field of Classification Search
CPC ........ A61M 5/007; A61M 5/30; A61M 5/178; A61M 5/31; A61M 5/1782; A61M 5/2046; A61M 5/482; A61M 5/20; A61M 5/3007; A61M 2005/3128; A61M 5/1408; A61M 2005/5046; A61M 2005/5053; A61M 2039/027; A61M 2039/064; A61M 2039/0646; A61B 2018/263
See application file for complete search history.

(56) References Cited

U.S. PATENT DOCUMENTS

| | | | |
|---|---|---|---|
| 6,063,053 A | | 5/2000 | Castellano et al. |
| 2002/0116021 A1* | | 8/2002 | Gordon .............. A61B 17/3203 606/167 |
| 2003/0171721 A1* | | 9/2003 | Enomoto .......... A61M 25/0075 604/247 |
| 2005/0173468 A1* | | 8/2005 | Matsumoto ........ B65D 47/2031 222/494 |
| 2007/0055214 A1* | | 3/2007 | Gilbert .................... A61M 5/30 604/500 |
| 2008/0097341 A1* | | 4/2008 | Casey ................. A61M 25/007 604/247 |
| 2011/0009815 A1* | | 1/2011 | Stormer-Talleur .......................... A61M 5/2033 604/68 |
| 2011/0282197 A1* | | 11/2011 | Martz ................. A61M 5/1782 600/432 |
| 2011/0284579 A1* | | 11/2011 | Pardes .................. A61M 39/22 222/207 |
| 2018/0154082 A1* | | 6/2018 | Yoh ..................... A61M 5/2046 |

FOREIGN PATENT DOCUMENTS

| | | |
|---|---|---|
| KR | 10-1052669 B1 | 7/2011 |
| KR | 10-1207977 B1 | 12/2012 |
| KR | 10-2014-0086919 A | 7/2014 |
| KR | 10-1684250 B1 | 12/2016 |
| KR | 10-1862201 B1 | 5/2018 |
| WO | 2011/126569 A1 | 10/2011 |
| WO | 2014/025241 A1 | 2/2014 |

OTHER PUBLICATIONS

International Search Report for PCT/KR2018/007492, dated Oct. 10, 2018.
Communication dated May 18, 2021, issued by the State Intellectual Property Office of the P.R.C. in application No. 201880035384.7.
The Extended European Search Report dated Apr. 23, 2021, issued by the European Patent Office in application No. 18852169.4.
Communication dated Feb. 28, 2022 from the Chinese Patent Office in Chinese Application No. 201880035384.7.

* cited by examiner

MICROJET DRUG INJECTION DEVICE EQUIPPED WITH BACKFLOW PREVENTION VALVE

TECHNICAL FIELD

The present invention relates to a microjet drug injection device equipped with a backflow prevention valve, and more particularly, to a microjet drug injection device equipped with a backflow prevention valve, which is equipped with a backflow prevention valve on the side of a lower housing in which a drug is filled, such that fluid is moved in one direction, thereby preventing the introduction of external air into the lower housing through an injection nozzle.

BACKGROUND ART

As a method of parenteral administration of therapeutic drugs in a patient's body, various drug delivery methods have been applied since ancient times. The most commonly used method for such a drug delivery system is a method using syringes. However, syringes have been feared by patients due to pain during injection, and have inevitable problems such as fear of infection due to wounds.

To solve this problem, drug delivery methods such as needleless syringes are being developed, and as a part of this research, drug delivery methods in which a drug is injected rapidly using a microjet method and penetrated directly into the body through the epidermis of skin are proposed.

For the high speed injection of such a microjet method, it is necessary to precisely and strongly inject a drug to the outside (i.e., skin). Such injection methods have been developed in various ways since the 1930s, and recently, various injection methods such as an injection method using a piezoelectric ceramic element, an injection method through a shock wave caused by applying a laser beam to an aluminum foil, and an injection method using a Lorentz force have been developed. In addition, unlike conventional microjet injection, a laser-bubble microjet injection method capable of continuously injecting and reusing while finely controlling the amount of drug to be injected and the injection speed of a drug (i.e., a penetration depth of the drug).

The laser-bubble microjet injection method applies a phenomenon that bubbles are generated by the collapse of a liquid structure when a strong energy such as a laser beam is concentrated in a liquid in a closed chamber. As the bubbles are generated and grown in the liquid in the closed space as described above, the total volume increases, and thus, an elastic membrane forming one side of the chamber is rapidly extended to the outside to push a drug solution out of a nozzle, thereby causing microjet injection.

However, there is a problem in that external air is introduced through the nozzle from which a drug is injected after the injection of the drug to contaminate the remaining drug.

Korean Patent No. 10-1207977 discloses a microjet drug delivery system.

DETAILED DESCRIPTION OF THE INVENTION

Technical Problem

The present invention is directed to a microjet drug injection device equipped with a backflow prevention valve for preventing external air from entering a lower housing through an injection nozzle and for automatically supplying a drug by providing a backflow prevention valve on the side of the lower housing to which a drug is filled to move fluid in one direction.

The objects of the one or more embodiments are not limited to the following description, and it should be understood by one of ordinary skill in the art that other objects not described here may be clearly understood from the following descriptions.

Technical Solution

According to an aspect of the present invention, a microjet drug injection device equipped with a backflow prevention valve, the microjet drug injection device comprises an upper housing sealed at one side of a pressure partition formed to surround the side and providing a floodlight lens at the sealed side; a lower housing comprising a drug partition formed to surround a side surface and an injection nozzle extending from the drug partition and comprising an injection path of drugs formed at a lower portion of the injection nozzle, wherein the lower housing is connected to or is extended from the upper housing; a compartment provided between the upper housing and the lower housing and partitioning a space in which a pressure generating liquid is filled in the upper housing and a space in which a drug is filled in the lower housing, and transmitting pressure acting on the space filled with the pressure generating liquid to the space in which a drug is filled; and a backflow prevention valve formed of an elastic material, wherein an upper side is provided in a lower side in the lower housing to be in close contact with the lower housing, an open circular inlet is formed on the upper side and the shape of the cross section, as the cross section goes downward, becomes gradually narrower as it changes from circular to linear, a lower end of the backflow prevention valve is formed with a slit through which a drug passes, allowing fluid to move only toward the injection nozzle, a pressure generating liquid is filled and sealed in a space on the side of the floodlight lens, and a drug filled in the space on the side of an injection nozzle is injected to the injection nozzle by pressure due to expansion of the pressure generating liquid.

According to an example embodiment, the microjet drug injection device of claim 1, wherein the backflow prevention valve is provided with a lower end cross-section and a slit shaped "C".

According to an example embodiment, in a lower portion of the backflow prevention valve, an inner material of the "C" shape has lower elastic modulus than an outer material of the "C" shape.

According to an example embodiment, the backflow prevention valve is provided with a lower end cross-section and a slit shaped "+".

According to an example embodiment, the microjet drug injection device comprises a plurality of injection paths.

According to an example embodiment, the injection paths are provided in a regular polygonal arrangement.

According to an example embodiment, an inner wall forming the injection path is formed of a ceramic material.

According to an example embodiment, diameter of the injection path is 50 micrometers to 250 micrometers.

Advantageous Effects of the Invention

According to a microjet drug injection device equipped with a backflow prevention valve of an embodiment of the present invention, external air may be prevented from flowing into a lower housing through an injection nozzle, and a drug may be automatically supplied after drug injection by providing a backflow prevention valve in a lower side of the lower housing to move fluid in one direction.

In addition, the shape of a lower end cross-section and a slit of the backflow prevention valve may be "C" shaped, whereby a sealing force may be increased and durability may be increased as compared with a case where the cross-section and the slit are straight.

In addition, since an inner material of the "C" shape of the backflow prevention valve is made of a material whose elastic modulus is less than that of an outer material, the slit may be opened more easily.

In addition, the shape of the lower end cross-section and the slit of the backflow prevention valve may be "+" shaped, whereby a sealing force may be increased and durability may be increased as compared with the case where the cross-section and the slit are straight. Also, the slit may be located close to an injection path and a drug may be pushed out at more uniform pressure.

In addition, by providing a plurality of injection paths, a procedure time may be shortened when multiple injections are required in an affected area.

In addition, by arranging the injection paths in a regular polygonal arrangement, drugs may be injected into the body at equal intervals.

In addition, by forming an inner wall of the injection path with a ceramic material, it is possible to improve durability by preventing the end of the injection path from being broken or deformed during the microjet injection.

In addition, by setting a diameter of the injection path to 50 to 250 micrometers, it is possible to minimize drug bounce off the surface of the skin while maintaining a sufficient skin injection depth of a drug.

DETAILED DESCRIPTION OF REFERENCE NUMERALS IN THE DRAWINGS

Figure 1:
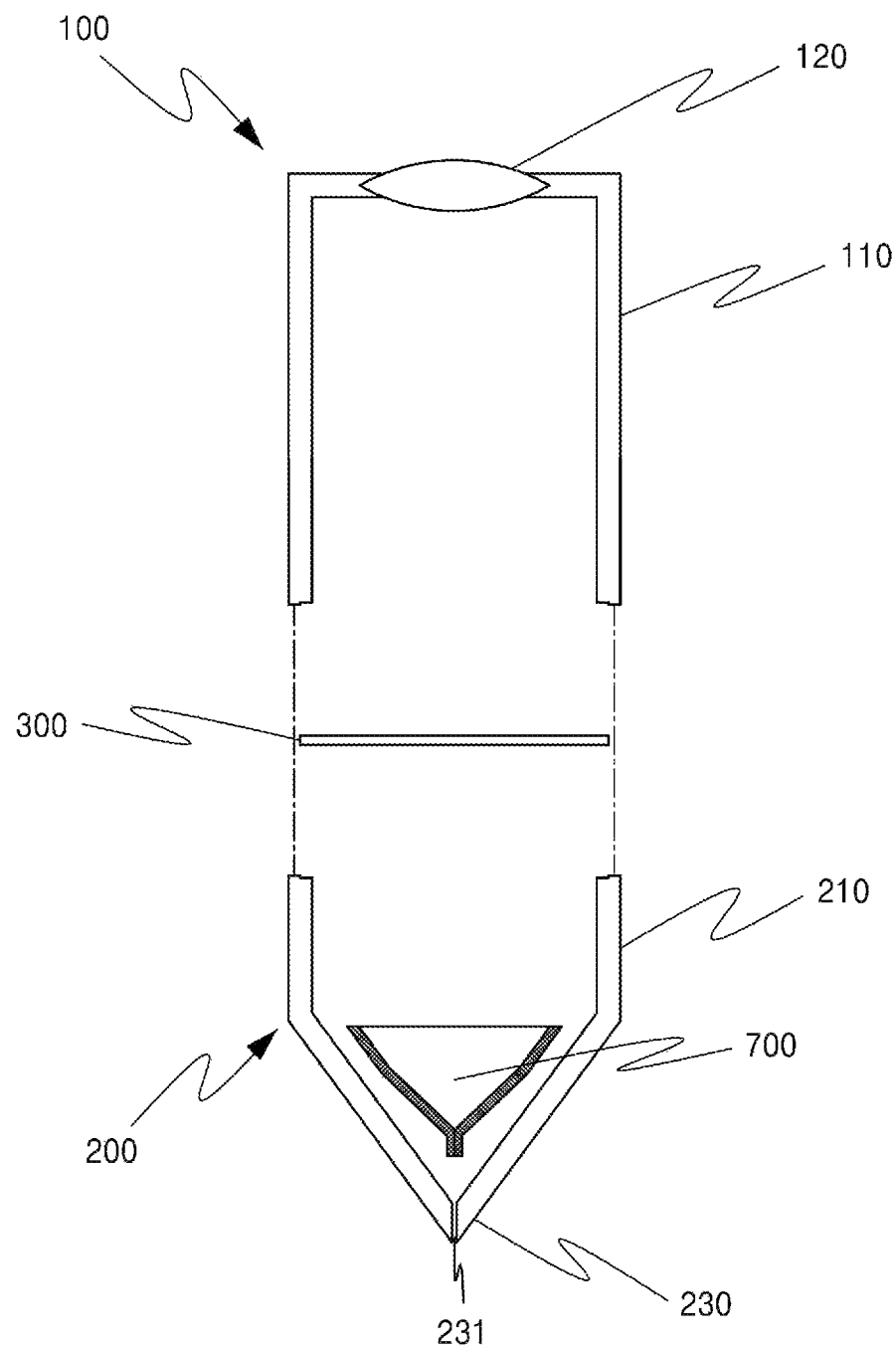
FIG. 1 is a view of an exploded concept of a microjet drug injection device equipped with a backflow prevention valve, according to an embodiment of the present invention.

100: upper housing
101: pressure generating liquid
110: pressure partition
120: floodlight lens
200: lower housing
210: drug partition
220: drug supplement
230: injection nozzle
231: injection path
300: compartment
500: energy intensive device
600: drug supply unit
700: backflow prevention valve

BEST MODE OF THE INVENTION

Since the present invention may have diverse modified embodiments, preferred embodiments are illustrated in the drawings and are described in the detailed description. However, this does not limit the present invention within specific embodiments and it should be understood that the present invention covers all the modifications, equivalents, and replacements within the idea and technical scope of the present invention.

Further, if it is described that one element is "connected" or "accesses" the other element, it is understood that the one element may be directly connected to or may directly access the other element but unless explicitly described to the contrary, another element may be "connected" or "access" between the elements.

However, if it is described that one element is "directly connected" or "directly accesses" the other element, it is understood that there are no other elements exists between them.

The terms used in this application, only certain embodiments have been used to describe, is not intended to limit the present invention. As used herein, the singular forms "a", "an", and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present invention will be described in detail with reference to the accompanying drawings. Prior to this, terms and words used in the present specification and claims should not be construed as limited to ordinary or dictionary meanings, but should be construed as meanings and concept consistent with the inventive concept based on the principle that the inventor can properly define the concept of terms in order to explain his or her invention in the best way. In addition, if there is no other definition in the technical terms and scientific terms used, it can be seen that they have a meaning that can be commonly understood by one of ordinary skill in the art. In the following description and the accompanying drawings, descriptions of well-known functions and configurations that may unnecessarily obscure the subject matter of the present invention will be omitted. The drawings introduced below are provided by way of example so as to fully convey the spirit of the present invention to one of ordinary skill in the art. Accordingly, the present invention is not limited to the drawings presented below and may be embodied in other forms. Also, like reference numerals refer to like elements throughout the specification. It should be noted that the same elements in the drawings are denoted by the same numerals wherever possible.

Figure 2:
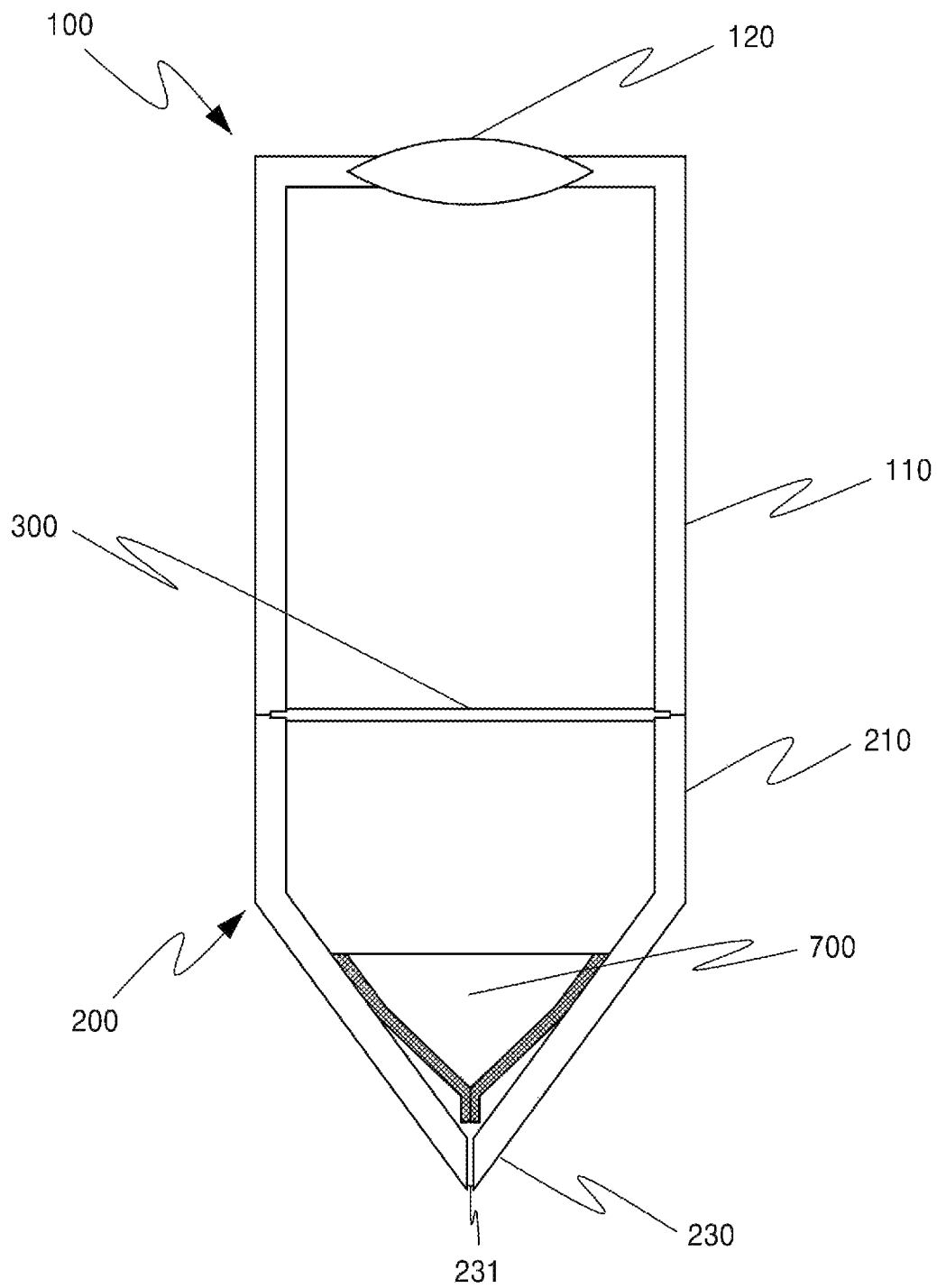
FIG. 2 is a view of a concept of assembling the microjet drug injection device of FIG. 1.
Figure 3:
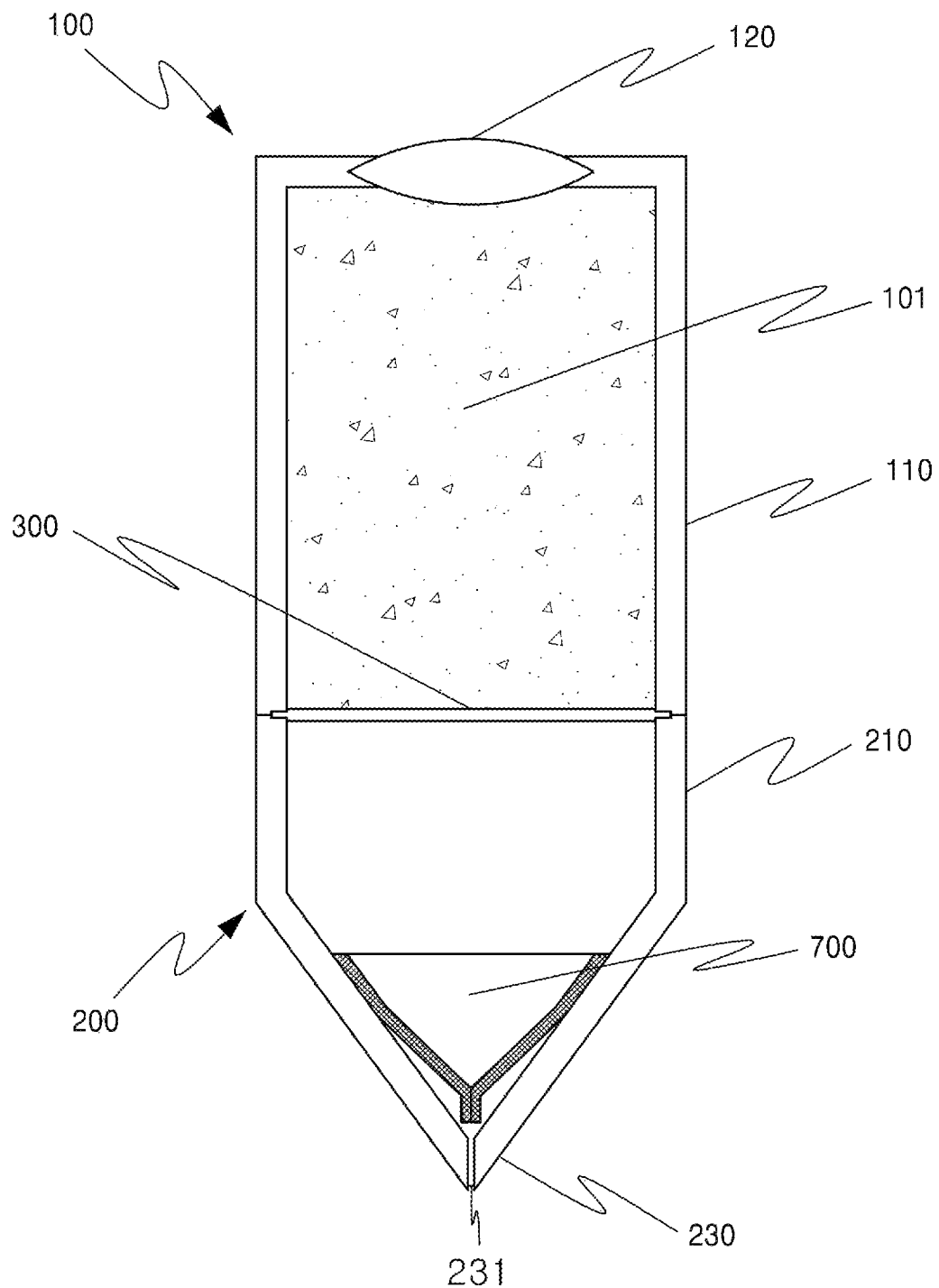
FIG. 3 is a view of a concept in which a pressure generating liquid is filled in the microjet drug injection device of FIG. 2.
Figure 4:
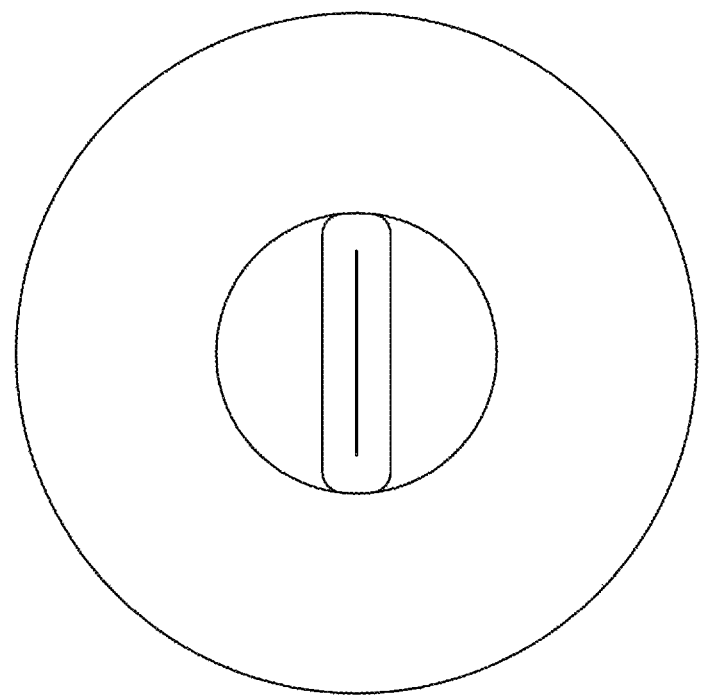
FIGS. 4 to 6 are plan views from below of each embodiment of a backflow prevention valve of FIG. 3.
Figure 5:
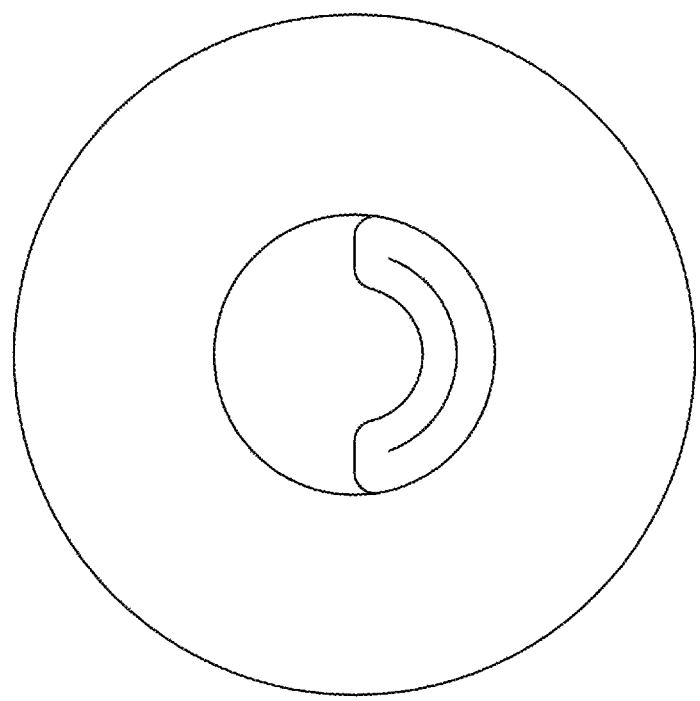
Figure 6:
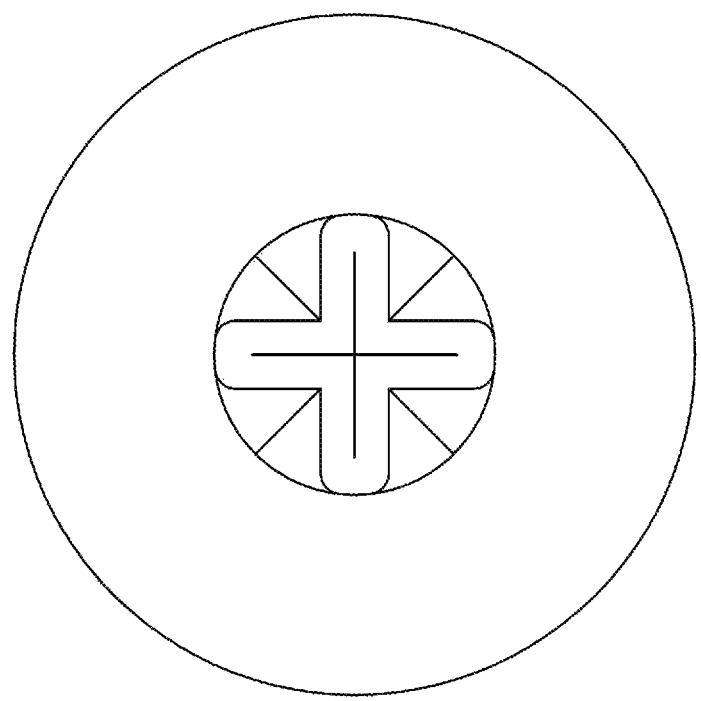
Figure 7:
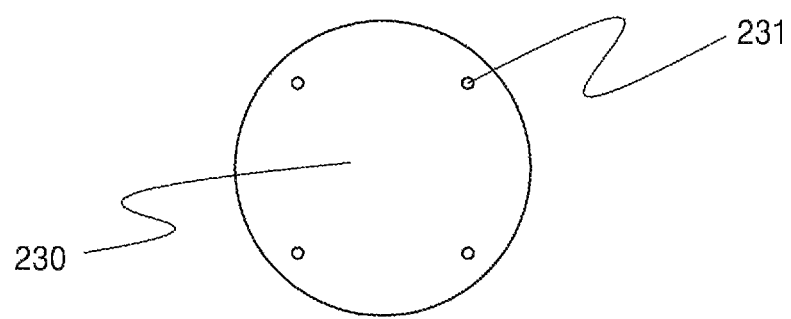
FIG. 7 is a plan view from below of an injection nozzle of FIG. 3.
Figure 8:
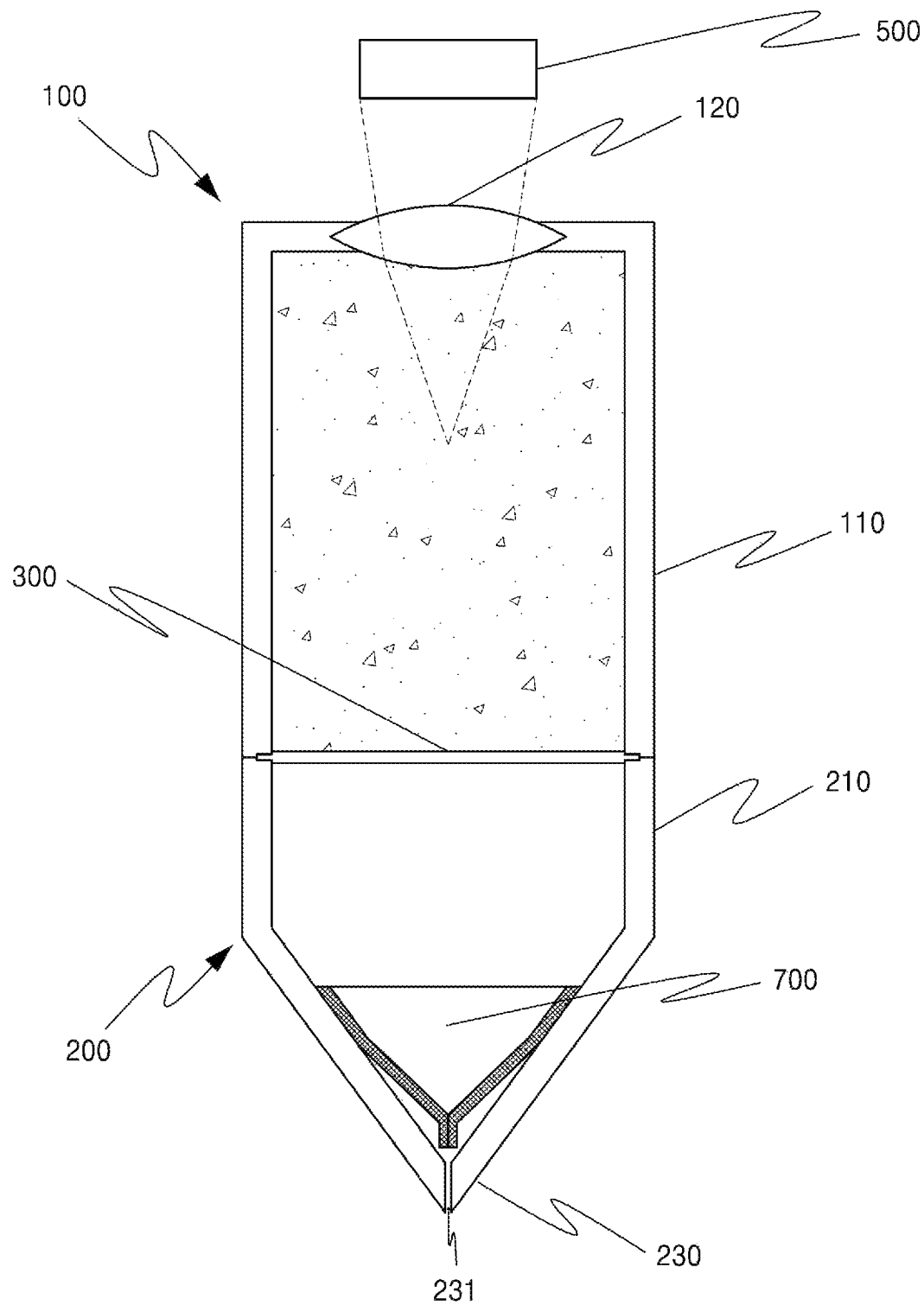
FIG. 8 is a view of a concept in which an energy intensive device is added to FIG. 3.
Figure 9:
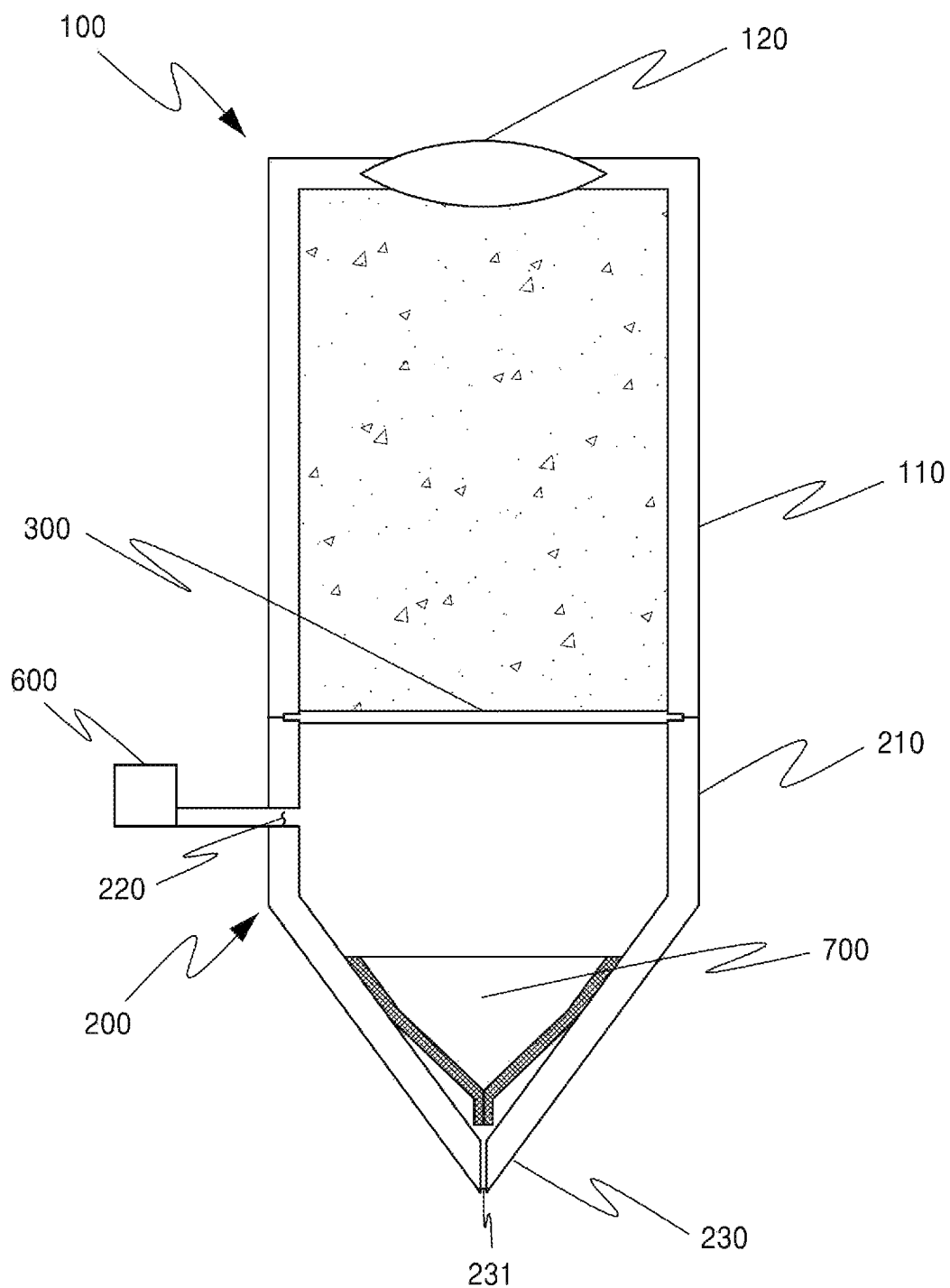
FIG. 9 is a view of a concept in which a drug supply unit is added to FIG. 3.

FIG. 1 is a view of an exploded concept of a microjet drug injection device equipped with a backflow prevention valve, according to an embodiment of the present invention. FIG. 2 is a view of a concept of assembling the microjet drug injection device of FIG. 1. FIG. 3 is a view of a concept in which a pressure generating liquid is filled in the microjet drug injection device of FIG. 2. FIGS. 4 to 6 are plan views from below of each embodiment of a backflow prevention valve of FIG. 3. FIG. 7 is a plan view from below of an injection nozzle of FIG. 3. FIG. 8 is a view of a concept in which an energy intensive device is added to FIG. 3. FIG. 9 is a view of a concept in which a drug supply unit is added to FIG. 3.

As illustrated in FIGS. 1 to 3, the microjet drug injection device equipped with a backflow prevention valve according to an embodiment of the present invention includes an upper housing 100 equipped with a floodlight lens 120, a lower housing 200, a compartment 300, and a backflow prevention valve 700, wherein a pressure generating liquid 101 is filled and sealed in a space on the side of the floodlight lens 120, and a drug filled in a space on the side of an injection nozzle 230 is injected to the injection nozzle 230 by pressure due to expansion of the pressure generating liquid 101.

The upper housing 100 is sealed at one side (upper side) of the pressure partition 110 formed to surround a side surface, and the floodlight lens 120 is provided at the sealed side.

The upper housing 100 is to form a closed space in which the pressure generating liquid 101 is filled, and forms a closed space in which the pressure generating liquid 101 is filled by blocking a side by the pressure partition 110, by blocking one side (the upper side in FIGS. 1 to 3) provided with the floodlight lens 120, and by blocking the other side by the partition 300 to be described later below.

FIGS. 1 to 3 show an example in which the floodlight lens 120 is expressed in a convex shape and blocks a portion of one side of the pressure partition 110, but the present invention is not limited thereto. As long as the light transmitting is possible, the floodlight lens 120 may have various shapes such as a planar shape and a concave shape. It is also possible to block the whole of one side of the pressure partition 110 with only the floodlight lens 120.

Normal water may be used as the pressure generating liquid 101, and various liquid materials such as polymer sol and gel such as alcohol or polyethylene glycol may be used. In addition, a degassed liquid may be preferably used as the pressure generating liquid 101 in order to minimize residual bubbles in generating bubbles. In addition, when an electrolyte (salt, etc.) is added to the pure water as the pressure generating liquid 101, molecules are ionized to reduce the energy required for the collapse of a molecular structure of a liquid, which is more preferable because bubbles may be formed with better efficiency.

The lower housing 200 includes a drug partition 210 formed to surround a side surface of the lower housing 200 and the injection nozzle 230 extending from the drug partition 210 and including an injection path 231 of drugs formed at a lower portion of the injection nozzle 230. The lower housing 200 is connected to or extended with the upper housing 100.

The lower housing 200 is for forming a space in which a drug is filled, and the drug partition 210, the injection nozzle 230, and the compartment 300 block other portions except the injection path 231 of drugs to form a space in which a drug is filled.

Here, the injection nozzle 230 refers to a portion in which the injection path 231 of drugs is formed, and may be all or a part of the inclined portion shown in FIGS. 1 to 3.

In this case, the upper housing 100 and the lower housing 200 may be integrally formed, or may be formed to be separated and coupled.

In addition, the injection nozzle 230 may be provided to be detachable to the lower housing 200. When the injection nozzle 230 is provided detachably to the lower housing 200, when the injection nozzle 230 is broken, contaminated, or clogged, it can be solved simply by replacing only the injection nozzle 230 without replacing the entire lower housing 200, which is advantageous in terms of cost.

Materials of a lower portion and a side portion of the lower housing 200 including the injection nozzle 230 may be variously selected as long as there is no problem in achieving the functions of the present invention, such as stellite, an aluminum alloy, and a zirconium-based ceramic material. Only a part of the lower portion of the lower housing 200 in which the injection path 231 is formed may be made of the zirconium-based ceramic material through insert injection.

Among zirconium-based ceramic materials, zirconium oxide (zirconia) has low thermal conductivity, which prevents the deterioration of a drug due to heat transfer during laser irradiation, and has high burst toughness and very high resistance to crack propagation, and thus it is possible to prevent a phenomenon in which ends of the injection path 231 and the like are damaged or deformed during microjet injection. Therefore, preferably, the lower housing 200, the injection nozzle 230, or the injection path 231 is formed of zirconium oxide (zirconia) in zirconium-based ceramic materials.

In addition, the lower housing 200 or the inside of the injection nozzle 230 has a larger horizontal cross-sectional area toward the upper side in some or all sections, and may include a plurality of sections in which inclination of an inner wall is constant for each predetermined section, but the inclination of the inner wall decreases toward the upper direction.

In addition, the lower housing 200 or the inside of the injection nozzle 230 may be provided in a trumpet shape that extends in a curved shape toward the compartment 300 from the injection path 231 in some or all sections.

The lower housing 200 or the inside of the injection nozzle 230 may further concentrate on pushing a drug into the injection path 231 by pressure transmitted from the compartment 300. Accordingly, the drug injected into the injection path 231 may obtain a larger injection speed.

The compartment 300 is provided between the upper housing 100 and the lower housing 200 and partitions a space in which a pressure generating liquid is filled of the upper housing 100 and a space in which a drug is filled of the lower housing 200, and transmits pressure acting on the space filled with the pressure generating liquid to the space in which a drug is filled.

That is, the compartment 300 partitions the upper housing 100 and the lower housing 200 to form a closed space in which the pressure generating liquid 101 is filled on one side of the compartment 300 (upper side of the compartment 300 of FIG. 2).

When the upper housing 100 and the lower housing 200 are formed to be separated and coupled, the compartment 300 is preferably interposed in a portion where the upper housing 100 and the lower housing 200 are connected to each other (see FIGS. 1 to 3).

The compartment 300 may be provided between the upper housing 100 and the lower housing 200, and may be formed of an elastic material that partitions the upper housing 100 and the lower housing 200.

In this case, the compartment 300 may be made of silicon rubber or the like.

The compartment 300 may be damaged first around the edge and the center due to rapid expansion. Therefore, the partition 300 preferably reinforces the edge and the center in preparation for rapid expansion.

In the above, the compartment 300 is a film formed of an elastic material, but the present invention is not limited thereto. If a plate-shaped disk is configured in the form of reciprocating up and down and may transmit the pressure acting on the space filled with the pressure generating liquid to the space in which a drug is filled, various implementations are possible.

The backflow prevention valve 700 is formed of an elastic (rubber) material, wherein the upper side is provided in a lower side of the lower housing 200 to be in close contact with the lower housing 200, and an open circular inlet is formed on the upper side and the shape of the cross section, as the cross section goes downward, becomes gradually narrower as it changes from circular to linear. A lower end of the backflow prevention valve 700 is formed with a slit through which a drug passes, allowing fluid to move only toward the injection nozzle 230.

The backflow prevention valve 700 allows the flow of fluid (liquid, gas, etc.) to flow in only one direction, and may be partially or entirely formed in a shape in which an entrance is closed like a duck's beak or a flute spout.

In addition, the backflow prevention valve 700, by allowing the drug filled in the lower housing 200 to be injected to the outside through the injection path 231 but preventing external air from being introduced through the injection path 231, may prevent the drug from being contaminated by preventing the external air from being mixed with the drug filled in the lower housing 200.

In more detail, the slit of the backflow prevention valve 700 is normally kept closed. The slit remains closed while a drug is filled in the lower housing 200. Subsequently, when the compartment 300 transmits the pressure to the side filled with a drug by the expansion of the pressure generating liquid 101, the slit is opened and the drug is injected through the injection path 231 by the pressure. In addition, when the pressure in the side filled with a drug is lowered and the injection of the drug is completed, the slit is closed by a restoring force (elastic force) of the backflow prevention valve 700 to prevent fluid from being sucked from the outside.

In this case, a linear shape in which the slit is closed may be applied to a straight line (see FIG. 3), a curve (see FIG. 4), an intersection line (see FIG. 5), etc.

As shown in FIG. 5, the backflow prevention valve 700 of the microjet drug injection device equipped with a backflow prevention valve according to an embodiment of the present invention may be characterized in that the lower end cross-section and the slit are "C" shaped.

When the lower end cross-section and the slit are "C" shaped, a sealing force may be increased so that the slit does not normally open as compared with the case where the cross-section and the slit are straight.

In addition, when the shape of the lower end cross-section and the slit are "C" shape, durability may be increased to increase the period of time that the slit does not normally open even if the slit is used continuously for a longer time as compared with the case where the shape of the cross section and the slit is a straight shape.

At this time, the lower portion of the backflow prevention valve 700 may be characterized in that an inner material of the "C" shape has lower elastic modulus than an outer material of the "C" shape.

This is to allow the slit of the backflow prevention valve 700 to be more easily opened by pressure caused by the expansion of the pressure generating liquid 101.

At this time, the ratio of elastic modulus of the inner material of the "C" shape and the outer material of the "C" shape is preferably about 0.6 to about 0.9:1.

As shown in FIG. 6, the backflow prevention valve 700 of the microjet drug injection device equipped with a backflow prevention valve according to an embodiment of the present invention may be characterized in that the lower end cross-section and the slit are "+" shaped.

When the lower end cross-section and the slit are "+" shaped, a sealing force may be increased so that the slit does not normally open as compared with the case where the cross-section and the slit are straight. In addition, the center of the slit may be on the extension line of the injection path 231 to minimize the maximum length of the slit so that the slit may be located near the injection path 231.

In addition, even when using the injection nozzle 230 provided with a plurality of injection paths 231 to be described later below, the injection nozzle 230 may push a drug at a more uniform pressure to each injection path 231.

Also, when the lower end cross-section and the slit are "+" shaped, durability may be increased to increase the period of time that the slit does not normally open even if the slit is used continuously for a longer time as compared with the case where the shape of the cross section and the slit is a straight shape.

The injection path 231 of the microjet drug injection device equipped with a backflow prevention valve according to an embodiment of the present invention may be plural.

The plurality of injection paths 231 may be provided in the lower portion of the lower housing 200. That is, only one injection path 231 may be provided, but two or more injection paths 231 may also be provided.

The number of injection paths 231 may be preferably 2 to 9.

In addition, an upper portion of each of the injection paths 231 may be formed in a tapered shape in which a horizontal cross-sectional area becomes narrower from the upper side to the lower side.

The microjet drug injection device provided with a backflow prevention valve according to an embodiment of the present invention having the plurality of injection paths 231 as described above is highly desirable because the microjet drug injection device may shorten a procedure time by injecting a drug into a wide area by a single microjet injection when several injections are required in a wide area.

As illustrated in FIG. 7, the injection paths 231 of the microjet drug injection device equipped with a backflow prevention valve according to an embodiment of the present invention may be provided in a regular polygonal arrangement.

The plurality of injection paths 231 may be provided in a regular polygonal arrangement such that the distance between neighboring injection paths 231 is constant, and thus drugs may be injected into the body at equal intervals during microjet injection.

Although FIG. 7 illustrates an example in which four injection paths 231 are provided in a square arrangement, the present invention is not limited thereto, and various embodiments such as rhombus forms are possible if the injection is possible at equal intervals.

An inner wall forming the injection path 231 of the microjet drug injection device equipped with a backflow prevention valve according to an embodiment of the present invention may be formed of a zirconium-based ceramic material (zirconia).

The inner wall forming the injection path 231 may be formed of a zirconium-based ceramic material and is preferably formed of zirconium oxide (zirconia). This is because, as mentioned above, zirconium oxide has high burst toughness and very high resistance to crack propagation, thereby preventing the end of the injection path 231 from being broken or deformed during the microjet injection.

The injection nozzle 230 formed of the zirconium-based ceramic material is provided to be detachable from the lower housing 200, and thus when the injection nozzle 230 provided with the injection path 231 is broken or when a change in the diameter of the injection path 231 is required, the injection nozzle 230 may be separated from the lower housing 200 so as to be replaced.

A diameter of the injection path 231 of the microjet drug injection device equipped with a backflow prevention valve according to an embodiment of the present invention may be 50 micrometers to 250 micrometers.

When the diameter of the injection path 231 is less than 50 micrometers, the amount of drug to be injected is small and the drug is not injected into the body to a sufficient depth. When the diameter of the injection path 231 exceeds 250 micrometers, the diameter of a microjet to which the drug is injected may increase, thereby increasing the amount of drug that is bounced off the surface of the skin and increasing the waste of the drug.

In addition, when the injection path 231 of drugs is formed to a diameter of 250 μm or less, even if a drug is filled in a space to be filled with a drug, if no pressure is applied above a certain level, the drug cannot escape through the injection path 231 of drugs.

As illustrated in FIG. 8, the microjet drug injection device provided with a backflow prevention valve according to an embodiment of the present invention may further include the energy intensive device 500 that concentrates energy toward a specific point in a closed space filled with the pressure generating liquid 101.

The energy intensive device 500 refers to a device capable of concentrating energy using a microwave, a laser beam, or the like.

That is, the energy concentrator 500 concentrates energy such as a laser beam in the pressure generating liquid 101 to push a drug into the injection path 231 of drugs by instantaneous volume expansion (pressure increase) due to evaporation of the pressure generating liquid 101 and delivery of shock waves, thereby generating a microjet.

As illustrated in FIG. 9, the microjet drug injection device provided with a backflow prevention valve according to an embodiment of the present invention may further include the drug supply unit 600 provided with the drug supplement 220 through which the drug partition 210 is formed to form a drug supply path and connected to the drug supplement 220 to supply a drug to a space on the side of the lower housing 200 through the drug supplement 220.

In other words, the drug supply unit 600 connected to the drug supplement 220 may be used to replenish a drug to the space to be filled with a drug.

The drug supply unit 600 may replenish a drug at a certain pressure at which a drug does not exit the injection path 231 of drugs.

This is to ensure that a drug is always filled without any control.

In other words, if there is no drug in a space to be filled with a drug, a drug is filled. However, if there is a drug in the space to be filled with a drug, a drug may be filled at a level that does not push the drug from the injection path 231 of drugs.

To describe the order in which a drug is replenished and injected, a drug is introduced into the lower housing 200 from the drug supply unit 600 through the drug supplement 220, and the drug in the lower housing 200 may be discharged to the outside through the injection path 231 to be injected in the form of a microjet. After the drug is injected, while the inflow of fluid to the injection path 231 is blocked by the backflow prevention valve 700, a drug may be refilled by a reduced pressure as the drug is injected.

By this circulation process, a drug may be automatically charged without a separate power supply or separate control.

In this case, all or a part of the inside of the lower housing 200 or the injection nozzle 230 may be formed in a tapered shape in which a horizontal cross-sectional area decreases from the compartment 300 toward the injection path 231. Through this, a pressure of the compartment 300 is concentrated in the injection path 231 to increase the injection speed of a microjet.

The present invention is not limited to the above-described embodiments and the scope of application is various, and various modifications may be made without departing from the subject matter of the present invention as claimed in the claims.

INDUSTRIAL APPLICABILITY

The present invention relates to a microjet drug injection device equipped with a backflow prevention valve, and may be usefully used in the art.

The invention claimed is:

1. A drug injection device, the drug injection device comprising:
   an upper housing in which at least one surface is sealed by a pressure partition;
   a lower housing, in which at least one surface is sealed by a drug partition, comprising an injection nozzle having an injection path formed at a lower portion;
   a partition provided between the upper housing and the lower housing to partition a space filled with a liquid for generating pressure at the upper housing and a space filled with a drug at the lower housing; and
   a backflow prevention valve provided with a slit formed at a lower end and configured to allow the drug, which is passed through the slit, to move only towards the injection nozzle,
   wherein, when the partition transmits the pressure to the space filled with the drug by an expansion of the liquid for generating pressure, the slit is configured to open such that the drug is injected through the injection nozzle,
   when the pressure in the space filled with the drug is lowered, a fluid is prevented from being sucked from an outside of the drug injection device while the slit is closed by a restoring force of the backflow prevention valve, and
   wherein in the backflow prevention valve, a cross section of the lower end and the slit forms a "C" shape, and an inner material of the "C" shape of the backflow prevention valve has smaller elastic modulus than an outer material of the "C" shape of the backflow prevention valve.

2. The drug injection device of claim 1, wherein the backflow prevention valve comprises an elastic material.

3. The drug injection device of claim 1, wherein the slit of the backflow prevention valve remains closed while the drug is filled inside the lower housing.

4. The drug injection device of claim 1, wherein the backflow prevention valve has an open circular inlet on an upper side, and the cross section becomes narrower toward a lower side to form a linear shape.

5. The drug injection device of claim 1, wherein a plurality of injection paths are provided.

6. The drug injection device of claim 5, wherein the plurality of injection paths form a regular polygonal arrangement.

7. The drug injection device of claim 1, wherein an inner wall forming the injection path comprises a ceramic material.

8. The drug injection device of claim 1, wherein a diameter of the injection path is 50 micrometers to 250 micrometers.

9. The drug injection device of claim 1, further comprising:
   a drug supply path through which the drug partition is formed to form a drug supply path; and
   a drug supply unit connected to the drug supply path to supply the drug to a space on a side of the lower housing through the drug supplement.

\* \* \* \* \*